| United States Patent [19] | [11] Patent Number: 4,924,015 |
|---|---|
| Howell et al. | [45] Date of Patent: May 8, 1990 |

[54] SUBSTITUTED ANTHRAQUINONES AND USE THEREOF IN EPOXY RESINS

[75] Inventors: Frederick H. Howell, Atherton, England; Rudolf Duthaler, Bettingen, Switzerland; Jürgen Finter, Freiburg, Fed. Rep. of Germany; Konrad Oertle, Therwil; Visvanathan Ramanathan, Basel, both of Switzerland

[73] Assignee: Ciba-Geigy Corporation, Ardsley, N.Y.

[21] Appl. No.: 208,526

[22] Filed: Jun. 20, 1988

[30] Foreign Application Priority Data

Jul. 1, 1987 [GB] United Kingdom ............... 87 15436

[51] Int. Cl.$^5$ .................... C07C 49/76; C07C 101/80; C07C 49/74
[52] U.S. Cl. .................................. 552/266; 552/708; 552/267
[58] Field of Search ............... 260/376, 383; 552/208, 552/266, 267

[56] References Cited

U.S. PATENT DOCUMENTS 4,657,842  4/1987  Finter et al.
4,855,084  8/1989  Dathaler et al. .................... 260/377

OTHER PUBLICATIONS

*chemical Abstracts*, vol. 90, No. 83, 8421, Utkina et al., 1978, "Quenoid Pigments from Echinodems".
*Chemical Abstracts*, vol. 90, No. 103, 705w, Imre et al., 1978, "New Alkylation Products of Quinizoni and its Monomethyl Ether".
Abrahart, *Dyes and Their Intermediates*, 1968, p. 8.

Primary Examiner—Richard L. Raymond
Assistant Examiner—R. Covington
Attorney, Agent, or Firm—Michael W. Glynn

[57] ABSTRACT

Anthraquinones having α,α-(dialkyl)alkyl groups which are functionally substituted, for example by —COOH or —CONH—NH$_2$, are described. Compositions which contain such anthraquinones, an aminoalcohol and an epoxy resin with or without a hardener are suitable for preparing metallic coatings and images on the cured composition by exposure to light and currentless metal deposition.

8 Claims, No Drawings

SUBSTITUTED ANTHRAQUINONES AND USE THEREOF IN EPOXY RESINS

The present invention relates to anthraquinones having functionally substituted α,α-(dialkyl)alkyl groups, to compositions which contain (a) such anthraquinones, (b) an amino alcohol, (c) an epoxy resin having on average more than one epoxy group in the molecule, and (d) if desired a hardener and the use of the cured composition for preparing metallic coatings or images.

EP-A No. 0,112,798 describes light-sensitive, cross-linked reaction products based on epoxy resins. In the presence of metal salts of groups Ib and VIII of the periodic table of the elements it is possible, through exposure to light, to produce metal seeds which can be thickened by currentless metal deposition. It is desirable to produce metallic coatings or images on light-sensitive epoxy resins by currentless metal deposition directly and without using metal salts.

The invention provides compounds of the formula I

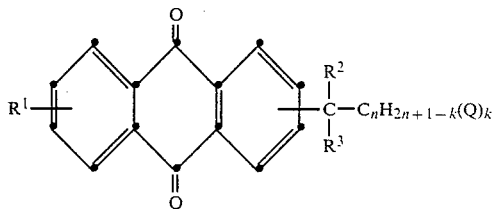

in which n is a number from 1 to 17, k is 1 or 2 and Q is —COOH or —CONR$^4$—NH$_2$ or k is 1 and Q is —OH, —NHR$^4$, —OCOR$^5$, —N(R$^4$)COR$^5$ or

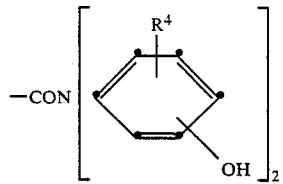

in which R$^4$ is H or C$_1$–C$_4$-alkyl and R$^5$ is a monodecarboxylated radical of a tricarboxylic acid or tetracarboxylic acid, R$^2$ and R$^3$ are independently of each other linear or branched C$_1$–C$_5$-alkyl which is unsubstituted or substituted by —COOH or —CONR$^4$—NH$_2$ if Q is —COOH or —CONR$^4$—NH$_2$, or R$^2$ together with the C$_n$H$_{2n+1-k}$ group forms C$_5$–C$_{12}$-cycloalkylene and R$^3$ is C$_1$–C$_5$-alkyl, and R$^1$ is H, linear or branched C$_1$–C$_8$-alkyl, unsubstituted or monohalogenated or dihalogenated C$_7$–C$_9$-aralkyl, unsubstituted or C$_1$–C$_4$-alkyl-substituted C$_5$–C$_{12}$-cycloalkyl, or a radical of the formula —CR$^2$R$^3$—C$_n$H$_{2n+1-k}$(Q)$_k$.

In the formula I, n is preferably a number from 1 to 12, in particular from 1 to 8, especially from 1 to 5, and k is preferably 1. In a preferred subgroup, n is a number from 1 to 8 and k=1.

Q is preferably —COOH and especially —CO—NR$^4$—NH$_2$ where R$^4$ is H or methyl. R$^5$ is preferably the radical of trimellitic acid or pyromellitic acid. In the radical

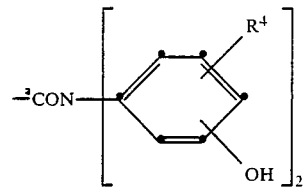

the —OH group is preferably bonded in the p-position, and R$^4$ is preferably H or methyl.

The group —CR$^2$R$^3$C$_n$H$_{2n+1-k}$(Q)$_k$ is preferably bonded to the anthraquinone in the 2-position, and the radical R$^1$ preferably in the 6- or 7-position. The radical R$^1$ is in this case in particular the group —CR$^2$R$^3$C$_n$H$_{2n+1-k}$(Q)$_k$.

R$^1$ is preferably H or the radical of the formula —CR$^2$R$^3$C$_n$H$_{2n+1-k}$(Q)$_k$. An alkyl R$^1$ preferably contains 1 to 4 C atoms. Examples of an alkyl R$^1$ are methyl, ethyl, n- and i-propyl, n-, i- and t-butyl, pentyl, hexyl, 2-ethylhexyl, heptyl and octyl. Aralkyl R$^1$ which can be substituted by halogen can be for example 1-phenyl-prop-1-yl, 1-phenylprop-2-yl, 1-phenylprop-3-yl, 1-phenyleth-1-yl, 1-phenylethy-2-yl, p-chlorobenzyl or in particular benzyl. A cycloalkyl R$^1$ preferably contains 5 or 6 ring C atoms; examples of R$^1$ in the meaning of cycloalkyl which can be substituted by alkyl are cyclopentyl, methylcyclohexyl, methylcyclopentyl, cyclohexyl, dimethylcyclohexyl, and butylcyclohexyl.

R$^2$ and R$^3$ are preferably independently of each other C$_1$–C$_3$-alkyl and in particular methyl or ethyl. R$^2$ and R$^3$ are preferably linear alkyl. R$^2$ can combine with the C$_n$H$_{2n-k}$ group to form cycloalkylene having preferably 5 or 6 ring C atoms, R$^3$ being C$_1$–C$_5$-alkyl, preferably C$_1$–C$_3$-alkyl.

R$^4$ in the meaning of alkyl can be for example butyl, propyl, ethyl or methyl. Preferably, R$^4$ is H or methyl.

A preferred subgroup of compounds of the formula I are those in which, in the formula I, R$^1$ is H or a radical of the formula —CR$^2$R$^3$C$_n$H$_{2n+1-k}$(Q)$_k$, R$^2$ and R$^3$ are independently of each other methyl or ethyl, n is a number from 1 to 8, k is 1, Q is —COOH or —CONR$^4$—NH$_2$, and R$^4$ is H or C$_1$–C$_4$-alkyl.

The invention further provides compounds of the formula Ia

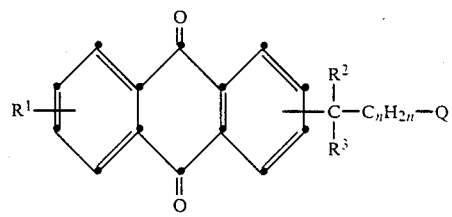

in which R$^1$ is H, linear or branched C$_1$–C$_8$-alkyl, unsubstituted or monohalogenated or dihalogenated C$_7$–C$_9$-aralkyl, unsubstituted or C$_1$–C$_4$-alkyl-substituted C$_5$–C$_{12}$-cycloalkyl or a radical of the formula —CR$^2$R$^3$—C$_n$H$_{2n}$—Q$^1$; R$^2$ and R$^3$ are independently of each other linear or branched C$_1$–C$_5$alkyl, or R$^2$ combines with the C$_n$H$_{2n}$ group to form C$_5$—C$_{12}$cycloalkylene and R$^3$ is H or C$_1$–C$_5$-alkyl; n is a number from 1 to 17, and Q$^1$ is —CN, —COCl, —CONHR$^4$, —CON(R$^4$)$_2$, —COR$^6$, —O—C$_1$–C$_8$-acyl or —NR$^4$—C$_1$–C$_8$-acyl in which R$^4$ is H or C$_1$–C$_4$-alkyl and R$^6$ is the radical of a monohydric alcohol. $R^1$ to $R^4$, n and k are subject to the same preferred meanings as for the compounds of the formula I. A radical $R^6$ of an monohydric alcohol preferably contains 1 to 12, in particular 1 to 6, C atoms. Examples of such radicals are methoxy, ethoxy, propoxy, butoxy, pentoxy, hexoxy, phenoxy, benzyloxy, octyloxy, decyloxy and dodecyloxy. The acyl can contain 1 to 8, preferably 1 to 4, C atoms. Examples of acyl are formyl, acetyl, propionyl, butanoyl, pentanoyl, hexanoyl and benzoyl. The compounds of the formula Ia are intermediates for preparing compounds of the formula I by a customary derivatization.

Examples of compounds of the formulae I and Ia are: 2-(3'-carboxy-2'-methyl-prop-2'-yl)-9,10-anthraquinone, 2-(3'-methoxycarbonyl-2'-methyl-prop-2'-yl)-9,10-anthraquinone, 2-(3'-ethoxycarbonyl-2'-methyl-prop-2'-yl)-9,10-anthraquinone, 2-(3'-propoxycarbonyl-2'-methyl-prop-2'-yl)-9,10-anthraquinone, 2-(3'-iso-propoxycarbonyl-2'-methyl-prop-2'-yl)-9,10-anthraquinone, 2-(3'-butoxycarbonyl-2'-methyl-prop-2'-yl)-9,10-anthraquinone, 2-(3'-hexyloxycarbonyl-2'-methyl-prop-2'-yl)-9,10-anthraquinone, 2-[3'-(2''-ethylhexyloxycarbonyl)-2'-methyl-prop-2'-yl]-9,10-anthraquinone, 2-(3'-dodecyloxycarbonyl-2'-methyl-prop-2'-yl)-9,10-anthraquinone, 2-(3'-octadecyloxycarbonyl-2'-methyl-prop-2'-yl)-9,10-anthraquinone, 2-(3'-carbamoyl-2'-methyl-prop-2'-yl)-9,10-anthraquinone, 2-(3'-carbohydrazido-2'-methyl-prop-2'-yl)-9,10-anthraquinone, 2-(4'-hydroxy-2'-methyl-but-2'-yl)-9,10-anthraquinone, 2-(4'-acetoxy-2'-methyl-but-2'-yl)-9,10-anthraquinone, 2-(4'-amino-2'-methyl-but-2'-yl)-9,10-anthraquinone, 2-(4'-acetamido-2'-methyl-but-2'-yl)-9,10-anthraquinone, 2-(4'-carbohydrazido-2'-methyl-but-2'-yl)-9,10-anthraquinone, 2-(4'-carboxy-2'-methyl-but-2'-yl)-9,10-anthraquinone, 2-(5'-carboxy-2'-methyl-pent-2'-yl)-9,10-anthraquinone, 2-(5'-methoxycarbonyl-2'-methyl-pent-2'-yl)-9,10-anthraquinone, 2-(5'-ethoxycarbonyl-2'-methyl-pent-2'-yl)-9,10-anthraquinone, 2-(5'-propoxycarbonyl-2'-methyl-pent-2'-yl)-9,10-anthraquinone, 2-(5'-iso-propoxycarbonyl-2'-methyl-pent-2'-yl)-9,10-anthraquinone, 2-(5'-butoxycarbonyl-2'-methyl-pent-2'-yl)-9,10anthraquinone, 2-(5'-hexyloxycarbonyl-2'-methyl-pent-2'-yl)-9,10-anthraquinone, 2-[5'-(2'''-ethylhexyloxycarbonyl)-2'-methyl-pent-2'-yl]-9,10-anthraquinone, 2-(5'-dodecyloxycarbonyl-2'-methyl-pent-2'-yl)-9,10-anthraquinone, 2-(5'-octadecyloxycarbonyl-2'-methyl-pent-2'-yl)-9,10-anthraquinone, 2-(5'-cyclohexyloxycarbonyl-2'-methyl-pent-2'-yl)-9,10-anthraquinone, 2-(5'-n-dec-10-enyloxycarbonyl-2'-methyl-pent-2'-yl)-9,10-anthraquinone, 2-(5'-benzyloxycarbonyl-2'-methyl-pent-2'-yl)-9,10-anthraquinone, 2-(5'-allyloxycarbonyl-2'-methyl-pent-2'-yl)-9,10-anthraquinone, 2-(5'-carbamoyl-2'-methyl-pent-2'-yl)-9,10-anthraquinone, 2-(5'-N,N-butylcarbamoyl-2'-methyl-pent-2'-yl)-9,10-anthraquinone, 2-(5'-N-allylcarbamoyl-2'-methyl-pent-2'-yl)-9,10-anthraquinone, 2-(5'-N,N-di-allylcarbamoyl-2'-methyl-pent-2'-yl)-9,10-anthraquinone, 2-(5'-N-benzylcarbamoyl-2'-methyl-pent-2'-yl)-9,10-anthraquinone, 2-(5'-cyano-2'-methyl-pent-2'-yl)-9,10-anthraquinone, 2-(5'-hydroxy-2'-methyl-pent-2'-yl)-9,10-anthraquinone, 2-(6'-amino-2'-methyl-hex-2'-yl)-9,10-anthraquinone, 2-(6'-acetamido-2'-methyl-hex-2'-yl)-9,10-anthraquinone, 2-(6'-amino-2'-methyl-hept-2'-yl)-9,10-anthraquinone, 2-(6'-acetamido-2'-methyl-hept-2'-yl)-9,10-anthraquinone, 2-(6'-hydroxy-2'-methyl-hex-2'-yl)-9,10-anthraquinone, 2-(6'-methoxy-2'-methyl-hex-2'-yl)-9,10-anthraquinone, 2-(6'-acetoxy-2'-methyl-hex-2'-yl)-9,10-anthraquinone, 2-(6'-chlorocarbonyl-2'-methyl-hex-2'-yl)-9,10-anthraquinone, 2-(5'-carbohydrazido-2'-methyl-pent-2'-yl)-9,10-anthraquinone, 2-(6'-cyano-2'-methyl-hex-2'-yl)-9,10-anthraquinone, 2-(6'-carboxy-2'-methyl-hex-2'-yl)-9,10-anthraquinone, 2-(6'-carbohydrazido-2'-methyl-hex-2'-yl)-9,10-anthraquinone, 2-(7'-carboxy-2',6'-dimethyl-hept-2'-yl)-9,10-anthraquinone, 2-(7'-methoxycarbonyl-2',6'-dimethyl-hept-2'-yl)-9,10-anthraquinone, 2-(7'-ethoxycarbonyl-2',6'-dimethyl-hept-2'-yl)-9,10-anthraquinone, 2-(7'-propoxycarbonyl-2',6'-dimethyl-hept-2'-yl)-9,10-anthraquinone, 2-(7'-iso-propoxycarbonyl-2',6'-dimethyl-hept-2'-yl)-9,10-anthraquinone, 2-(7'-butoxycarbonyl-2',6'-dimethyl-hept-2'-yl)-9,10-anthraquinone, 2-(7'-hexyloxycarbonyl-2',6'-dimethyl-hept-2'-yl)-9,10-anthraquinone, 2-[5'-(2''-ethylhexyloxycarbonyl-2',6'-dimethyl-hept-2'-yl]-9,10-anthraquinone, 2-(5'-dodecyloxycarbonyl-2',6'-dimethyl-hept-2'-yl)-9,10-anthraquinone, 2-(5'-octadecyloxycarbonyl-2',6'-dimethyl-hept-2'-yl)-9,10-anthraquinone, 2-(7'-carbamoyl-2',6'-dimethyl-hept-2'-yl)-9,10-anthraquinone, 2-(8'-amino-2',6'-dimethyl-oct-2'-yl)-9,10-anthraquinone, 2-(8'-acetamido-2',6'-dimethyl-oct-2'-yl)-9,10-anthraquinone, 2-(7'-cyano-2',6'-dimethyl-hept-2'-yl)-9,10-anthraquinone, 2-(8'-hydroxy-2',6'-dimethyl-oct-2'-yl)-9,10-anthraquinone, 2-(8'-acetoxy-2',6'-dimethyl-oct-2'-yl)-9,10-anthraquinone, 2-(8'-carboxy-2',6'-dimethyl-oct-2'-yl)-9,10-anthraquinone, 2-(8'-n-benzyloxycarbonyl-2',6'-dimethyl-oct-2'-yl)-9,10-anthraquinone, 2-(8'-n-methylamino-2',6'-dimethyl-oct-2'-yl)-9,10-anthraquinone, 2-(8'-chlorocarbonyl-2',6'-dimethyl-oct-2'-yl)-9,10-anthraquinone, 2-(8'-cyano-2',6'-dimethyl-oct-2'-yl)-9,10-anthraquinone, cis and trans 2-(4'-carboxy-1'-methyl-cyclo-hex-1'-yl)-9,10-anthraquinone, cis and trans 2-(4'-methoxycarbonyl-1'-methyl-cyclo-hex-1'-yl)-9,10-anthraquinone, 2,6-bis-(3'-carboxy-2'-methyl-prop-2'-yl)-9,10-anthraquinone, 2,7-bis-(3'-carboxy-2'-methyl-prop-2'-yl)-9,10-anthraquinone, 2,6-bis-(3'-methoxycarbonyl-2'-methyl-prop-2'-yl)-9,10-anthraquinone, 2,7-bis-(3'-methoxycarbonyl-2'-methyl-prop-2'-yl)-9,10-anthraquinone, 2,6-bis-(3'-ethoxycarbonyl-2'-methyl-prop-2'-yl)-9,10-anthraquinone, 2,7-bis-(3'-ethoxycarbonyl-2'-methyl-prop-2'-yl)-9,10-anthraquinone, 2,6-bis-(3'-propoxycarbonyl-2'-methyl-prop-2'-yl)-9,10-anthraquinone, 2,7-bis-(3'-propoxycarbonyl-2'-methyl-prop-2'-yl)-9,10-anthraquinone, 2,6-bis-(3'-iso-propoxycarbonyl-2'-methyl-prop-2'-yl)-9,10-anthraquinone, 2,7-bis-(3'-isopropoxycarbonyl-2'-methyl-prop-2'-yl)-9,10-anthraquinone, 2,6-bis-(3'-butoxy-carbonyl-2'-methyl-prop-2'-yl)-9,10-anthraquinone, 2,7-bis-(3'-butoxycarbonyl-2'-methyl-prop-2'-yl)-9,10-anthraquinone, 2,6-bis-(3'-hexyloxycarbonyl-2'-methyl-prop-2'-yl)-9,10-anthraquinone, 2,7-bis-(3'-hexyloxycarbonyl-2'-methyl-prop-2'-yl)-9,10-anthraquinone, 2,6-bis-[3'-(2''-ethylhexyloxycarbonyl)-2'-methyl-prop-2'-yl]-9,10-anthraquinone, 2,7-bis-[3'-(2''-ethylhexyloxycarbonyl)-2'-methyl-prop-2'-yl]-9,10-anthraquinone, 2,6-bis-(3'-dodecyloxycarbonyl-2'-methyl-prop-2'-yl)-9,10-anthraquinone, 2,7-bis-(3'-dodecyloxycarbonyl-2'-methyl-prop-2'-yl)-9,10-anthraquinone, 2,6-bis-(3'-octadecyloxycarbonyl-2'-methyl-prop-2'-yl)-9,10-anthraquinone, 2,7-bis-(3'-octa-decyloxycarbonyl-2'-methyl-prop-2'-yl)-9,10-anthraquinone, 2,6-bis-(4'-hydroxy-2'-methyl-but-2'-yl)-9,10-anthraquinone, 2,7-bis-(4'-hydroxy-2'-methyl-but-2'-yl)-9,10-anthraquinone, 2,6-bis-(4'-acetoxy-2'-methyl-but-2'-yl)-9,10-anthraquinone, 2,7-bis-(4'-acetoxy-2'-methyl-but-2'-yl)-9,10-anthraquinone, 2,6-bis-(5'-carboxy-2'-methyl-pent-2'-yl)-9,10-anthraquinone, 2,7-bis-(5'-carboxy-2'-methyl-pent-2'-yl)-9,10-anthraquinone, 2,6-bis-(5'-methoxycarbonyl-2'-methyl-pent-2'-yl)-9,10-anthraquinone, 2,7-bis-(5'-methoxycarbonyl-2'-methyl-pent-2'-yl)-9,10-anthraquinone, 2,6-bis-(5'-ethoxycarbonyl-2'-methyl-pent-2'-yl)-9,10-anthraquinone, 2,7-bis-(5'-ethoxycarbonyl-2'-methyl-pent-2'-yl)-9,10-anthraquinone, 2,6-bis-(5'-propoxycarbonyl-2'-methyl-pent-2'-yl)-9,10-anthraquinone, 2,7-bis-(5'-propoxycarbonyl-2'-methyl-pent-2'-yl)-9,10-anthraquinone, 2,6-bis-(5'-isopropoxycarbonyl-2'-methyl-pent-2'-yl)-9,10anthraquinone, 2,7-bis-(5'-isopropoxycarbonyl-2'-methyl-pent-2'-yl)-9,10-anthraquinone, 2,6-bis-(5'-butoxycarbonyl-2'-methyl-pent-2'-yl)-9,10-anthraquinone, 2,7-bis-(5'-butoxycarbonyl-2'-methyl-pent-2'-yl)-9,10-anthraquinone, 2,6-bis-(5'-hexyloxycarbonyl-2'-methyl-pent-2'-yl)-9,10-anthraquinone, 2,7-bis-(5'-hexyloxycarbonyl-2'-methyl-pent-2'-yl)-9,10-anthraquinone, 2,6-bis-[5'-(2''-ethylhexyloxycarbonyl)-2'-methyl-pent-2'-yl]-9,10-anthraquinone, 2,7-bis-[5'-(2'''-ethylhexyloxycarbonyl)-2'-methyl-pent-2'-yl]-9,10-anthraquinone, 2,6-bis-(5'-carbohydrazido-2'-methyl-pent-2'-yl)-9,10-anthraquinone, 2,7-bis-(5'-carbohydrazido-2'-methyl-pent-2'-yl)-9,10-anthraquinone, 2,6-bis-(5'-octadecyloxycarbonyl-2'-methyl-pent-2'-yl)-9,10-anthraquinone, 2,7-bis-(5'-octadecyloxycarbonyl-2'-methyl-pent-2'-yl)-9,10-anthraquinone, 2,6-bis-(5'-cyano-2'-methyl-pent-2'-yl)-9,10-anthraquinone, 2,7-bis-(5'-cyano-2'-methyl-pent-2'-yl)-9,10-anthraquinone, 2,6-bis-(6'-hydroxy-2'-methyl-hex-2'-yl)-9,10-anthraquinone, 2,7-bis-(6'-hydroxy-2'-methyl-hex-2'-yl)-9,10-anthraquinone, 2,6-bis-(6'-acetoxy-2'-methyl-hex-2'-yl)-9,10-anthraquinone, 2,7-bis-(6'-acetoxy-2'-methyl-pent-2'-yl)-9,10-anthraquinone, 2,6-bis-(5'-carbamoyl-2'-methyl-pent-2'-yl)-9,10-anthraquinone, 2,7-bis(5'-carbamoyl-2'-methyl-pent-2'-yl)-9,10-anthraquinone, 2,6-bis-(5'-N-methylcarbamoyl-2'-methyl-pent-2'-yl)-9,10-anthraquinone, 2,7-bis-(5'-N-methylcarbamoyl-2'-methyl-pent-2'-yl)-9,10-anthraquinone, 2,6-bis-(5'-N,N-dimethylcarbamoyl-2'-methyl-pent-2'-yl)-9,10-anthraquinone, 2,7-bis-(5'-N,N-dimethylcarbamoyl-2'-methyl-pent-2'-yl)-9,10-anthraquinone, 2,6-bis-(5'-N-n-butylcarbamoyl-2'-methyl-pent-2'-yl)-9,10-anthraquinone, 2,7-bis-(5'-N-n-butylcarbamoyl-2'-methyl-pent-2'-yl)-9,10-anthraquinone, 2,6-bis-(6'-cyano-2'-methyl-hex-2'-yl)-9,10-anthraquinone, 2,7-bis-(6'-carboxy-2'-methyl-hex-2'-yl)-9,10-anthraquinone, 2,6-bis-(6'-chlorocarbonyl-2'-methyl-hex-2'-yl)-9,10-anthraquinone, 2,7-bis-(6'-amino-2'-methyl-hex-2'-yl)-9,10-anthraquinone, 2,6-bis-(6'-carbohydrazido-2'-methyl-hex-2'-yl)-9,10-anthraquinone, 2,6-bis-(7'-carboxy-2',6'-dimethyl-hept-2'-yl)-9,10-anthraquinone, 2,7-bis-(7'-carboxy-2',6'-dimethyl-hept-2'-yl)-9,10-anthraquinone, 2,6-bis-(7'-methoxycarbonyl-2',6'-dimethyl-hept-2'-yl)-9,10-anthraquinone, 2,7-bis-(7'-methoxycarbonyl-2',6'-dimethyl-hept-2'-yl)-9,10-anthraquinone, 2,6-bis-(7'-cyano-2',6'-dimethyl-hept-2'-yl)-9,10-anthraquinone, 2,7-bis-(7'-cyano-2',6'-dimethyl-hept-2'-yl)-9,10-anthraquinone, 2,6-bis-(8'-hydroxy-2',6'-dimethyl-oct-2'-yl)-9,10-anthraquinone, 2,7-bis-(8'-hydroxy-2',6'-dimethyl-oct-2'-yl)-9,10-anthraquinone, 2,6-bis-(8'-acetoxy-2',6'-dimethyl-oct-2'-yl)-9,10anthraquinone, 2,7-bis-(8'-acetoxy-2',6'-dimethyl-oct-2'-yl)-9,10-anthraquinone, 2,6-bis-(8'-cyano-2',6'-dimethyl-oct-2'-yl)-9,10-anthraquinone, 2,7-bis-(8'-cyano-2',6'-dimethyl-oct-2'-yl)-9,10-anthraquinone, 2,6-bis-(8'-carboxy-2',6'-dimethyl-oct-2'-yl)-9,10-anthraquinone, 2,7-bis-(8'-carboxy-2',6'-dimethyl-oct-2'-yl)-9,10-anthraquinone, 2,6-bis-(8'-amino-2',6'-dimethyl-oct-2'-yl)-9,10-anthraquinone, 2,7-bis-(8'-amino-2',6'-dimethyl-oct-2'-yl)-9,10-anthraquinone, 2,6-bis-(8'-carbohydrazido-2',6'-dimethyl-oct-2'-yl)-9,10-anthraquinone, 2,7-bis-(8'-carbohydrazido-2',6'-dimethyl-oct-2'-yl)-9,10-anthraquinone, 2,6 and 2,7-bis-(4'-carboxy-1'-methyl-cyclo-hex-1'-yl)-9,10-anthraquinone, 2,6 and 2,7-bis-(4'-methoxycarbonyl-1'-methyl-cyclo-hex-1'-yl)-9,10-anthraquinone, 2,6-bis-(5'-cyclohexyloxycarbonyl-2'-methyl-pent-2'-yl)-9,10-anthraquinone, 2,7-bis-(5'-cyclohexyloxycarbonyl-2'-methyl-pent-2'-yl)-9,10-anthraquinone, 2-methyl-6-(5'-methoxycarbonyl-2'-methyl-pent-2'-yl)-9,10-anthraquinone, 2-methyl-7-(5'-methoxycarbonyl-2'-methyl-pent-2'-yl)-9,10-anthraquinone, 2-ethyl-6-(5'-methoxycarbonyl-2'-methyl-pent-2'-yl)-9,10-anthraquinone, 2-ethyl-7-(5'-methoxycarbonyl-2'-methyl-pent-2'-yl)-9,10-anthraquinone, 2-t-butyl-6-(5'-carboxy-2'-methyl-pent-2'-yl)-9,10-anthraquinone, 2-t-butyl-7-(5'-carboxy-2'-methyl-pent-2'-yl)-9,10-anthraquinone, 2-t-butyl-6-(5'-methoxycarbonyl-2'-methyl-pent-2'-yl-9,10-anthraquinone, 2-t-butyl-7-(5'-methoxycarbonyl-2'-methyl-pent-2'-yl)-9,10-anthraquinone, 2-t-butyl-6-(5'-ethoxycarbonyl-2'-methyl-pent-2'-yl)-9,10-anthraquinone, 2-t-butyl-7-(5'-ethoxycarbonyl-2'-methyl-pent-2'-yl)-9,10-anthraquinone, 2-t-butyl-6-(5'-propoxycarbonyl-2'-methyl-pent-2'-yl)-9,10-anthraquinone, 2-t-butyl-7-(5'-propoxycarbonyl-2'-methyl-pent-2'-yl)-9,10-anthraquinone, 2-t-butyl-6-(5'-isopropoxycarbonyl-2'-methyl-pent-2'-yl)-9,10-anthraquinone, 2-t-butyl-7-(5'-isopropoxycarbonyl-2'-methyl-pent-2'-yl)-9,10-anthraquinone, 2-t-butyl-6-(5'-n-butoxycarbonyl-2'-methyl-pent-2'-yl)-9,10-anthraquinone, 2-t-butyl-7-(5'-n-butoxycarbonyl-2'-methyl-pent-2'-yl)-9,10-anthraquinone, 2-t-butyl-6-(5'-n-hexyloxycarbonyl-2'-methyl-pent-2'-yl)-9,10-anthraquinone, 2-t-butyl-7-(5'-n-hexyloxycarbonyl-2'-methyl-pent-2'-yl)-9,10-anthraquinone, 2-t-butyl-6-[5'-(2'''-ethylhexyloxycarbonyl)-2'-methyl-pent-2'-yl]-9,10-anthraquinone, 2-t-butyl-7-[5'-(2'''-ethylhexyloxycarbonyl)-2'-methyl-pent-2'-yl]-9,10-anthraquinone, 2-t-butyl-6-(carbohydrazido-2'-methyl-pent-2'-yl)-9,10-anthraquinone, 2-t-butyl-7-(carbohydrazido-2'-methyl-pent-2'-yl)-9,10-anthraquinone, 2-t-butyl-6-(cyclohexyloxycarbonyl-2'-methyl-pent-2'-yl)-9,10-anthraquinone, 2-t-butyl-7-(cyclohexyloxycarbonyl-2'-methyl-pent-2'-yl)-9,10-anthraquinone, 2-t-butyl-6-(5'-carbamoyl-2'-methyl-pent-2'-yl)-9,10-anthraquinone, 2-t-butyl-7-(5'-carbamoyl-2'-methyl-pent-2'-yl)-9,10-anthraquinone, 2-(1',1',3',3'-tetramethylbutyl)-6-(5'-methoxycarbonyl-2'-methyl-pent-2'-yl)-9,10-anthraquinone, 2-(1',1',3',3'-tetramethylbutyl)-7-(5'-methoxycarbonyl-2'-methyl-pent-2'-yl)-9,10-anthraquinone 2-cumyl-6-(5'-methoxy'-methyl-pent-2'-yl)-9,10-anthraquinone, 2-cumyl-7-(5'-methoxycarbonyl-2'-methyl-pent-2'-yl)-9,10-anthraquinone, 2-(1'-methyl-cyclohex-1'-yl)-6-(5'-methoxycarbonyl-2'-methyl-pent-2'-yl)-9,10-anthraquinone, 2-(1'-methyl-cyclohex-1'-yl)-7-(5'-methoxycarbonyl-2'-methyl-pent-2'-yl)-9,10-anthraquinone, 2-t-butyl-6-(7'-methoxycarbonyl-2',6'-dimethyl-hept-2'-yl)-9,10-anthraquinone, 2-t-butyl-7-(7'-methoxycarbonyl-2',6'-dimethyl-hept-2'-yl)-9,10-anthraquinone, 2-t-butyl-6-(7'-cyano-2',6'-dimethyl-hept-2'-yl)-9,10-anthraquinone, 2-t-butyl-7-(7'-cyano-2',6'-dimethyl-hept-2'-yl)-9,10-anthraquinone, 2-t-butyl-6-(8'-hydroxy-2',6'-dimethyl-oct-2'-yl)-9,10-anthraquinone, 2-t-butyl-7-(8'-hydroxy-2',6'-dimethyl-oct-2'-yl)-9,10-anthraquinone, 2-t-butyl-6-(8'-acetoxy-2',6'-dimethyl-oct-2'-yl)-9,10-anthraquinone, 2-t-butyl-7-(8'-acetoxy-2',6'-dimethyloct-2'-yl)-9,10-anthraquinone, cis- and trans 2-t-butyl-6-(4'-methoxycarbonyl-1'-methyl-cyclohex-1'-yl)-9,10- anthraquinone, cis- and trans 2-t-butyl-7-(4′-methoxycarbonyl-1′-methyl-cyclohex-1′-yl)-9,10-anthraquinone and 2-(5,5-dimethoxycarbonyl)-2′-methyl-pent-2′-yl)-9,10-anthraquinone.

The compounds of the formula I and Ia can be prepared by processes known per se, which comprise (a) oxidizing an anthracene of the formula II

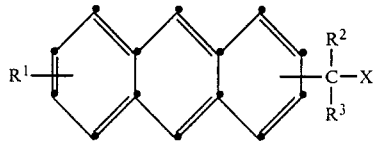
(II)

in which X is —$C_nH_{2n+1-k}(Q)_k$ or —$C_nH_{2n}$ n-$Q^1$ and $R_1$, $R^2$, $R^3$, Q, $Q^1$, n and k are as defined above, to a compound of the formula I or Ia, or (b) reacting a substituted benzene of the formula III or IIIa

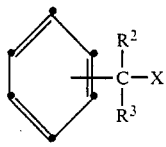
(III)

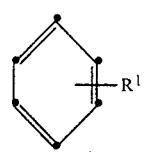
(IIIa)

with a phthalic anhydride of the formula IV or IVa

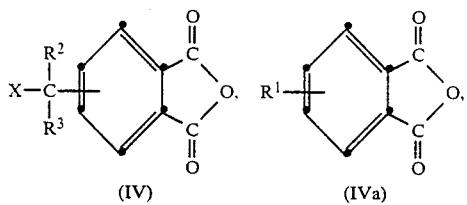
(IV)        (IVa)

to give benzophenone compounds of the formula V, Va or Vb

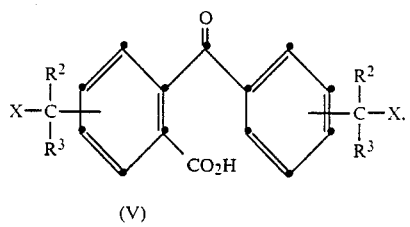
(V)

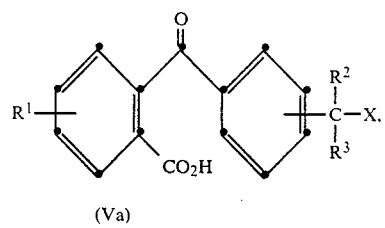
(Va)

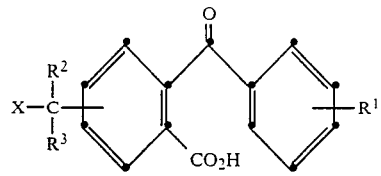
(Vb)

and subsequently cyclizing the benzophenone compounds to the compounds of the formula I or Ia.

The oxidation of the anthracenes can be effected by means of chromic or nitric acid, or catalytically by means of oxygen in the presence of vanadium pentoxide. The preparation of anthracenes of formula II is described for example in EP-A No. 0,174,271.

The reaction of the benzenes of the formulae III and IIIa with the anhydrides of the formulae IV and IVa is known and is carried out in general using AlCl$_3$ as catalyst. The cyclization of the benzophenone compounds of the formula V, Va or Vb can be effected in a known manner, for example using oleum. It can be advantageous to protect the functional group Q or $Q^1$. It is also possible to prepare compounds of the formulae I by transforming a functional group Q or $Q^1$ in a known way into another functional group.

The substituted benzenes of the formulae III and IIIa are known or can be obtained by customary alkylating processes for benzene. The phthalic acids of the formulae IV and are known or preparable by conventional methods. For instance, o-xylene can be alkylated, Specifically functionally alkylated, in a known manner and subsequently oxidized to give the correspondingly substituted phthalic acids from which the substituted anhydrides can be prepared by dehydration. Alternatively, it is possible for example to react 2-benzoylaniline under Friedel-Crafts conditions with a functional alkylating agent to give a compound of the formula

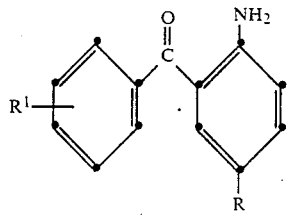

The diazotization and subsequent reaction with NaCN/CuCN leads to the nitrile, the hydrolysis of which gives the carboxylic acid which can be cyclized to compounds of the formula I or Ia. Suitable functional alkylating agents are for example tertiary alcohols and branched alkenes having functional groups Q or $Q^1$. The compounds of the formulae V, Va and Vb are novel and form a further part of the subject-matter of the invention.

The compounds of the formula I are suitable for preparing light-sensitive cured epoxy resins. The invention further provides a curable composition containing (a) at least one epoxy resin having on average more than one epoxy group in the molecule,
(b) if desired a hardener for the epoxy resin,
(c) an anthraquinone of the formula I according to claim 1 or mixtures thereof and (d) at least one primary or secondary aliphatic amine which contains in the aliphatic radical at least one hydroxyl group.

The epoxy resin preferably contains on average at least 2 epoxy groups in the molecule.

Suitable epoxy resins are in particular those having on average more than one glycidyl, β-methylglycidyl or 2,3-epoxycyclopentyl group bonded to a hetero atom (e.g. sulfur, preferably oxygen or nitrogen); examples being in particular bis-(2,3-epoxycyclopentyl) ether, di- or polyglycidyl ethers of polyhydric aliphatic alcohols, such as 1,4-butanediol, or polyalkylene glycols, such as polypropylene glycols, di- or polyglycidyl ethers of cycloaliphatic polyols, such as 2,2-bis-(4-hydroxycyclohexyl)-propane, di- or polyglycidyl ethers of polyhydric phenols, such as resorcinol, tris-(p-hydroxyphenyl)-methane, 2,2-bis-(p-hydroxyphenyl)-propane (=diomethane), 2,2-bis-(4'-hydroxy-3',5'-dibromophenyl)propane, 1,1,2,2-tetrakis-(p-hydroxyphenyl)-ethane; or of condensation products obtained under acid conditions of phenols with formaldehyde such as phenol novolaks and cresol novolaks, di- or poly-(β-methylglycidyl) ethers of the abovementioned polyhydric alcohols or polyhydric phenols, polyglycidyl esters of polybasic carboxylic acids, such as phthalic acid, terephthalic acid, $\Delta^4$-tetrahydrophthalic acid and hexahydrophthalic acid, N-glycidyl derivatives of amines, amides and heterocyclic nitrogen bases, such as N,N-diglycidylaniline, N,N-diglycidyltoluidine, N,N,O-triglycidyl-p-aminophenol, N,N,N',N'-tetraglycidyl-bis-(p-aminophenyl)methane, triglycidyl isocyanurate, N,N'-diglycidylethyleneurea, N,N'-diglycidyl-5,5-dimethylhydantoin, N,N'-diglycidyl-5-isopropylhydantoin, N,N-methylene-bis-(N',N'-diglycidyl)-5,5-dimethylhydantoin, 1,3-bis-(N-glycidyl-5,5-dimethylhydantoin)-2-glycidyloxypropane and N,N'-diglycidyl-5,5-dimethyl-6-isopropyl-5,6-dihydro-uracil.

A preferred group of epoxy resins are glycidylated novolaks, hydantoins, aminophenols, bisphenols or aromatic diamines. Particularly preferred compositions contain as epoxy resin a glycidylated cresol novolak, bisphenol-A diglycidyl ether, bisphenol-A diglycidyl ethers advanced with bisphenol A, hydantoin N,N'-bis-glycide, propylene-1,3-bis-hydantoin 2-hydroxytriglycide, p-aminophenol triglycide, diaminodiphenylmethane tetraglycide or mixtures thereof.

Also suitable are prereacted adducts of such epoxides with hardeners for epoxides, for example the abovementioned adduct of bisphenol-A diglycidyl ether and bisphenol A.

Suitable hardeners for epoxy resins are acid or basic compounds. Example of suitable hardeners are: amines such as aliphatic, cycloaliphatic or aromatic, primary, secondary or tertiary amines, e.g. ethylenediamine, hexamethylenediamine, trimethylhexamethylenediamine, diethylenetriamine, triethylenetetramine, tetraethylenepentamine, N,N-dimethylpropylene-1,3-diamine, N,N-diethylpropylene-1,3-diamine, 2,2-bis-(4'-aminocyclohexyl)-propane, 3,5,5-trimethyl-3-(aminomethyl)-cyclohexylamine ("isophoronediamine"), Mannich bases, such as 2,4,6-tris-(dimethylaminomethyl)-phenol, m-phenylenediamine, p-phenylenediamine, bis-(4-aminophenyl)-methane, bis-(4-aminophenyl) sulfone, m-xylylenediamine, adducts of acrylonitrile or monoepoxides, e.g. ethylene oxide or propylene oxide on polyalkylenepolyamines, e.g. diethylenetriamine or triethylenetetramine, adducts of polyamines, e.g. diethylenetriamine or triethylenetetramine, in excess and polyepoxides, e.g. diomethane polyglycidyl ethers, adducts of monophenols or polyphenols and polyamides, polyamides, in particular those based on aliphatic polyamines, e.g. diethylenetriamine or triethylenetetramine, and dimerized or trimerized unsaturated fatty acids, e.g. dimerized linseed oil fatty acid (VERSAMID®), polysulfides (THIOKOL®), aniline-formaldehydes, polyhydric phenols, e.g. resorcinol, 2,2-bis-(4-hydroxyphenyl)-propane or phenol-formaldehyde resins, polybasic carboxylic acids and anhydrides thereof, e.g. phthalic anhydride, $\Delta^4$-tetrahydrophthalic anhydride, hexahydrophthalicanhydride, 4-methylhexahydrophthalic anhydride, 3,6-endomethylene- $\Delta^4$-tetrahydrophthalic anhydride, 4-methyl-3,6-endomethylene-$\Delta^4$-tetrahydrophthalic anhydride (=methylnadic anhydride), 3,4,5,6,7-hexa-chloro-3,6-endomethylene-$\Delta^4$-tetrahydrophthalic anhydride, succinic anhydride, adipic anhydride, trimethyladipic anhydride, azelaic anhydride, sebacic anhydride, maleic anhydride, dodecylsuccinic anhydride, pyromellitic dianhydride, trimellitic anhydride, benzophenonetetracarboxylic dianhydride or mixtures of such anhydrides.

A preferred group of hardeners are novolaks, polyamines and carboxylic anhydrides.

The composition according to the invention can also contain curing accelerants or thermal or photochemical curing catalysts. Examples are: tertiary amines, salts thereof or quaternary ammonium compounds, e.g. 2,4,6-tris-(dimethylaminomethyl)-phenol, benzyldimethylamine, 2-ethyl-4-methylimidazole, triamylammonium phenolate, mono- or polyphenols such as phenol or diomethane or salicylic acid, dicyanodiamide, boron trifluoride and its complexes with organic compounds, such as $BF_3$-ether complexes and $BF_3$-amine complexes, e.g. $BF_3$-monoethylamine complex, acetoacetanilide-$BF_3$ complex, phosphoric acid, triphenyl phosphite. Suitable photosensitive curing accelerants are onium salts or metal complexes, for example diazonium salts, of aromatic amines, triphenylsulfonium or diphenyliodonium salts or cyclopentadienylironarene salts.

Curing accelerants and catalysts are customarily added in an amount of 0.1–10% by weight, based on the epoxy resin. Hardeners for epoxy resins are generally used in equimolar amounts, based on the epoxy groups and functional groups of a hardener.

The composition preferably contains the anthraquinone of the formula I in an amount of 0.1–1, in particular 0.2–0.8, mol/kg of epoxy resin, and the hydroxyl-containing amine preferably in an amount of 0.1–1.2, in particular 0.3–1, mol/ kg of epoxy resin. Additional hardeners are preferably present in an amount of 0.1–0.5, in particular 0.1–0.3 mol/kg of epoxy resin.

The amines of component (d) can be hydroxyl-containing aliphatic amines having 2 to 30, preferably 2 to 20, C atoms and 1 to 3, preferably 1, hydroxyl group in the aliphatic radical. The aliphatic radical can be linear or branched and interrupted by —O— or amino groups. Preferably, the aliphatic radical contains primary OH groups. In a preferred embodiment, the amine conforms to the formula VI

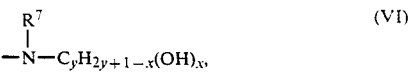

in which $R^7$ is H, linear or branched $C_1$-$B_{18}$-alkyl, $C_3$-$C_7$-cycloalkyl, $C_6$-$C_{10}$-aryl, $C_7$-$C_{18}$-alkaryl, $C_7$-$C_{12}$-aralkyl, $C_8$-$C_{18}$-alkaralkyl or the group —$C_yH_{2y+1-x}OH_x$, x is a number from 1 to 3 and y is a number from 2 to 12, it being possible for the group $C_yH_{2y}$ to be interrupted by one or more —O— or —$NR^7$.

An alkyl $R^7$ preferably contains 1 to 12, in particular 1 to 6, C atoms. An alkyl $R^7$ is preferably methyl or ethyl. $R^7$ is in particular H. A cycloalkyl $R^7$ preferably contains 5 or 6 ring C atoms and is for example cyclopentyl or cyclohexyl.

An aryl $R^7$ can be for example naphthyl and in particular phenyl. An aralkyl $R^7$ is in particular $C_7$-$C_{18}$-alkylphenyl, for example methylphenyl, ethylphenyl, dimethylphenyl, n- and i-propylphenyl, n-, i- and t-butylphenyl, pentylphenyl, hexylphenyl, octylphenyl, nonylphenyl, decylphenyl or dodecylphenyl. An aralkyl $R^7$ can be 1- or 2-phenyleth-1-yl or in particular benzyl. An alkaralkyl $R^7$ is preferably alkylbenzyl having in particular 8 to 14 C atoms, e.g. methylbenzyl, ethylbenzyl, dimethylbenzyl, n- and i-propylbenzyl, n-, i- and t-butylbenzyl, pentylbenzyl or hexylbenzyl. A group $C_yH_{2y}$ interrupted by —O— can be oxaalkylene radicals which can conform for example to the formula —$R^8$—$(OR^9)_t$—, where $R^8$ and $R^9$ are independently of each other linear or branched $C_2$-$C_6$-alkylene and t is a number from 2 to 6. A group $C_yH_{2y}$ interrupted by —$NR^7$— can preferably conform to the formula —(—$R^{10}$—NH—)$_s$—$R^{11}$— where $R^{10}$ is linear or branched $C_2$-$C_6$-alkylene, preferably ethylene, $R^{11}$ is linear or branched $C_1$-$C_{10}$-alkylene, preferably $C_2$-$C_6$-alkylene, and s is a number from 1 to 3. In the formula VI, y is in particular a number from 2 to 7.

A preferred subgroup are those amines of the formula VI in which $R^7$ is H, y is a number from 2 to 7 and x a number from 1 to 3.

Examples of amines of the formula VI are: ethanolamine, 1-amino-2-hydroxypropane, 1-amino-3-hydroxypropane, 1-amino-4-hydroxybutane, 1-amino-5-hydroxypentane, 1-amino-6-hydroxyhexane, aminotrimethylolmethane, aminodimethylolmethane, aminomethyldimethylolmethane, aminomethyltrimethylolmethane, hydroxyethoxyethylamine, hydroxypropoxyethylamine, N-(hydroxyethyl)ethylenediamine, N-(hydroxyethyl)-diethylenetriamine, $H_2N(CH_2CH_2O—)_{2-6}$-H.

Primary aliphatic hydroxyl-containing amines are hardeners for epoxy resins, linear polymers being obtained when epoxy resins having 2 epoxy groups are used. If other hardeners are used as well, crosslinked polymers are obtained.

In the compositions according to the invention, preference is given to using anthraquinones of the formula I when $R^1$ is H, $R^2$ and $R^3$ are independently of each other methyl or ethyl, k is 1, n is a number from 1 to 5, and Q is —CO—$NR^4$—$NH_2$ in which $R^4$ is H or methyl.

In the compositions according to the invention, the anthraquinones conform very especially to the formula

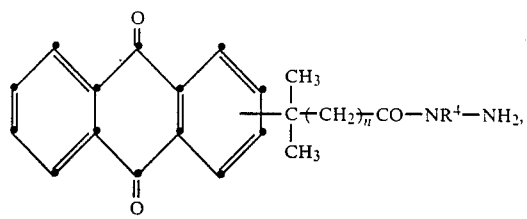

in which n is a number from 1 to 3 and $R^4$ is H or methyl.

When using the monofunctional anthraquinones of the formula I it is advantageous to use epoxy resins having at least 3 epoxy groups in the molecule, for example epoxidized novolaks, to obtain crosslinked epoxy resins.

The compositions according to the invention are curable, the cured or crosslinked epoxy resins being light-sensitive. Areas of the surface which are exposed to light can be coated with thin layers of metals, e.g. copper, by currentless metal deposition.

The composition is cured in a known manner, possibly concomitantly with or after a shaping in the conventional manner, for example the preparation of coatings on a base material by spraying, spread-coating or knife-coating, or the preparation of shaped articles by means of casting techniques, or the preparation of composites by impregnating and pressing.

The hydroxyl-containing amine of component (d) can in a preferred embodiment be prereacted with the epoxy resin of component (a) to give adducts and then be mixed with an anthraquinone of the formula I acting as a hardener, with or without hardeners for epoxy resins, and crosslinked. Suitable hardeners from anthraquinones of the formula I are in particular those difunctional anthraquinones where, in the formula I, $R^1$ is a radical —$CR^2R^3C_nH_{2n}$ n(Q) and Q is —OH, —$NHR^4$ or —COOH, or where $R^1$ is H, alkyl, aralkyl or cycloalkyl and Q is —CO—$NR^4$—$NH_2$, —$OCOR^5$, —$NHR^4$ or

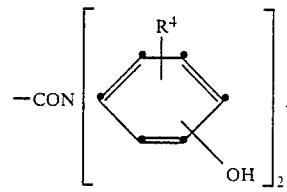

Particular preference is given to the hydrazides of monocarboxylic acids of the formula I.

When using monofunctional anthraquinones of the formula I in which $R^1$ is H, alkyl, aralkyl or cycloalkyl and Q is —OH, —$NHR^4$ or —COOH, it can be advantageous to use a hardener for epoxy resins as well, in particular a novolak, amine or anhydride hardener. Advantageously, the monofunctional anthraquinone is prereacted together with the OH-containing amine and the epoxide and then mixed with a hardener and cured.

In addition to a curing in stages, it is also possible to mix together all the components and then to effect curing.

The components are mixed together by customary processing methods in the presence or absence of a solvent. It is also possible to add further additives customary for the processing or improving the properties of the cured epoxy resins, for example plasticizers, dyes, pigments, fillers, mould release agents or H-donors. To deposit metals, the presence of metal salts or metal complexes of group Ib or VIII of the periodic table of the elements can be advantageous, for example in an amount of 0.01 to 10% by weight, based on the composition. The curing is generally effected at temperatures of 20° to 200° C., in particular 50° to 150° C. The cured compositions comprise a further part of the subject-matter of the invention.

The cured compositions are light-sensitive. The areas exposed to light appear darker than the unexposed areas. The exposed areas can be directly coated with metals from conventional metal deposition baths (see for example U.S. Pat. No. 4,510,279), in particular those containing for example nickel or copper salts. In this way it is possible for example to produce printed circuits. The exposed epoxy resins can also be used for optical recordings.

The invention further provides a method of using a cured composition according to the invention for preparing metallic coatings or images by currentless metal deposition after exposing the surface to light as a whole or in parts.

Exposure is preferably effected with UV light. It is possible to use any desired light sources, although the use of UV lamps is preferable. Suitable light sources are for example xenon lamps, metal halide lamps and in particular mercury high pressure and medium pressure lamps.

The metallic coatings or images can be prepared as follows: the composition according to the invention, which can be present as a layer on a base material, is cured according to the invention, then exposed to light areawise or through an image original, and thereafter treated with a metal deposition bath.

The use of a metal salt or metal complex is superfluous. The deposited metals adhere firmly to the epoxy resin surface; a pretreatment is not necessary. Furthermore, the cured compositions have increased glass transition temperatures.

The examples which follow illustrate the invention in more detail. Parts are by weight. Ether is diethyl ether.

(A) Preparation of substituted anthraquinones

EXAMPLE 1

Methyl 5-(2'-anthraquinoyl)-5-methylhexanecarboxylate (a) 8.9 parts of anthracene, 14.2 parts of methyl 5-methyl-5-hexenecarboxylate and 26.1 parts of stannic chloride are mixed with 50 parts of xylene and heated on a steam bath for 24 hours. The reaction mixture is then poured into 250 parts of 2N hydrochloric acid, and the organic phase is extracted with ether. The ether solution is then washed in succession with water, aqueous sodium carbonate and water, and the ether is evaporated off. The residue is taken up in methanol, and the undissolved anthracene (3.7 parts) is filtered off. The methanol solution is subjected to reduced pressure to distil off the methanol. The residue is distilled. A fraction having a boiling point of 220° C./0.7 mbar is obtained. Crystallization of the fraction from 40°–60° C. petroleum ether gives methyl 5-(2'-anthracenyl)-5-methylhexenoate having a melting point of 82°–84° C.

(b) 7.1 parts of this compound and 50 parts of glacial acetic acid are added together, stirred and heated on a steam bath. A solution of 5 parts of chromium trioxide in 5 parts of water and 20 parts of glacial acetic acid is added dropwise in the course of 30 minutes. This is followed by a further 30 minutes of heating. The glacial acetic acid is then distilled off on a rotary evaporator under reduced pressure. The residue is diluted with water, the organic phase is extracted with ether, the ether solution is washed with water, and the ether is evaporated. Distillation of the residue gives a fraction boiling at 230°–240° C./0.4 mbar. The distillate is diluted with 40°–60° C. petroleum ether which contains a little ether, and the precipitate is filtered off and dried. This gives methyl 5-(2'-anthraquinoyl)-5-methylhexanecarboxylate having a melting point of 72°–74° C.

(c) Alkaline hydrolysis gives 5-(2'-anthraquinoyl)-5-methylhexanecarboxylic acid having a melting point of 125°–127° C. (recrystallized from ether).

EXAMPLE 2

5-(2'-Anthraquinoyl)-5-methyl-pentane-1-nitrile (a) Methyl 5-(2'-anthracenyl)-5-methylhexanecarboxylate as per Example 1a gives on alkaline hydrolysis 5-(2'-anthracenyl)-5-methylhexanecarboxylic acid having a melting point of 149°–151° C. (recrystallized from glacial acetic acid/water).

(b) 8.2 parts of this compound are mixed with 8.2 parts of urea and maintained at 190° C. for 3.5 hours. After cooling down, the mixture is taken up in acetone and filtered. The acetone is evaporated off, and the residue is taken up in ethyl acetate. The solution is washed with aqueous sodium bicarbonate and water. The ethyl acetate is then evaporated off, and the residue is taken up in 40°–60° C. petroleum ether. The precipitate is filtered off and dried. This gives 5-(2'-anthracenyl)-5-methylhexanecarboxamide having a melting point of 142°–144° C.

(c) 1.7 parts of this compound are heated together with 1.6 parts of phosphorus pentoxide at 195° C. for 4 hours. After cooling down, the reaction mass is extracted with ethyl acetate, the extract is filtered, and the ethyl acetate is evaporated. The residue is subjected to a short-path distillation at 220° C./0.13 mbar, and the distillate is recrystallized from ethyl acetate. This gives 5-(2'-anthracenyl)-5-methyl-pentane-1-nitrile having a melting point of 111°–115° C.

(d) 0.2 part of this compound is dissolved in 5 parts of acetone and then treated with 2 parts of Jones reagent. The reaction mixture is set aside for 5 minutes and then poured into water. This is followed by extraction with ether, washing the ether solution with water, evaporating the ether and subjecting the residue to a short-path distillation. This gives 5-(2'-anthraquinoyl)-5-methyl-pentane-1-nitrile as a red oil.

| | Elemental analysis (% by weight): | | |
| --- | --- | --- | --- |
| | C | H | N |
| Found: | 79.44 | 6.23 | 4.06 |
| Calculated: | 79.47 | 6.03 | 4.41 |

EXAMPLE 3

N-[5-(2'-Anthraquinoyl)-5-methylhex-1-yl]-acetamide (a) 90 parts of borane-tetrahydrofuran complex (1M solution in tetrahydrofuran) are stirred, and 5 parts of compound as per 2b are added portionwise in the course of 30 minutes. This is followed by 3 hours of heating under reflux, cooling down and the addition of 60 parts of 6M hydrochloric acid. The tetrahydrofuran is removed under reduced pressure, and the aqueous phase is treated with sodium carbonate solution and then extracted with ethyl acetate. The ethyl acetate solution is washed with water, the ethyl acetate is evaporated, and the residue dissolved in 10 parts of toluene and treated with 2 parts of acetic anhydride. This is followed by heating on a steam bath for 30 minutes and removal of the volatiles on a rotary evaporator under reduced pressure. The oily residue is digested with ether/40°–60° C. petroleum ether. The crystalline precipitate is filtered off and dried. The product obtained is N-[5-(2'-anthracenyl)-5-methylhex-1-yl]acetamide having a melting point of 90°–93° C.

(b) 0.5 part of this compound is dissolved in 25 parts of acetone and treated with a Jones reagent until an orange brown colour persists. The acetone is removed under reduced pressure, and water is added to the residue. This is followed by extraction with ether, washing with water and evaporation of the ether. This leaves a red oil, which is diluted with ether and a little acetone. The precipitate formed is filtered off and dried. The product obtained is N-[5-(2'-anthraquinoyl)-5-methylhex-1-yl]acetamide having a melting point of 112°–113° C.

EXAMPLE 4

8-(2'-Anthraquinoyl)-2,6-dimethyloctan-1-ol (a) 8.9 parts of anthracene, 19.8 parts of citronellyl acetate, 13 parts of stannic chloride and 1.5 parts of trifluoromethanesulfonic acid are mixed with 50 parts of p-xylene and heated on a steam bath for 8 hours. After cooling, the reaction mixture is poured into dilute hydrochloric acid, which is followed by extraction with ether. The extract is washed with water, evaporated and distilled. This gives a fraction having a boiling point of 220°–280° C./0.78 mbar, which is chromatographed over silica using 40°–60° C. petroleum ether. Elution with petroleum ether containing 2% by volume of ether gives 8-(2'-anthracenyl)-2,6-dimethyl-1-acetoxyoctane as a pale yellow oil.

| Elemental analysis (% by weight): | | |
|---|---|---|
| | C | H |
| Found: | 82.65 | 8.76 |
| Calculated: | 82.94 | 8.57 |

(b) The compound is oxidized with Jones reagent as described in Example 2d and worked up to give 8-(2'-anthraquinoyl)-2,6-dimethyl-1-acetoxy-octane as a viscous yellow oil.

| Elemental analysis (% by weight): | | |
|---|---|---|
| | C | H |
| Found: | 76.80 | 7.17 |
| Calculated: | 76.82 | 7.44 |

(c) Alkaline hydrolysis of this compound gives 8-(2'anthraquinoyl)-2,6-dimethyloctan-1-ol as a yellow viscous oil.

| Elemental analysis (% by weight): | | |
|---|---|---|
| | C | H |
| Found: | 79.01 | 7.77 |
| Calculated: | 79.09 | 7.74 |

EXAMPLE 5

2,6-Bis(5-carboxy-2-methyl-pent-2-yl)anthraquinone (a) 26.1 parts of anhydrous stannic chloride are dissolved in 100 parts of p-xylene. 1.5 parts of trifluoromethanesulfonic acid, 14.2 parts of methyl 5-methylhex-5-enecarboxylate and 17.8 parts of anthracene are added. The mixture is heated on a steam bath for 8 hours and, after cooling down, is poured into 500 parts of water. This is followed by extraction with ether, washing of the ether solution with water and evaporation of the ether. The residue has added to it 300 parts of methanol, and the mixture is brought to the reflux and then filtered. The filtrate is treated with 1 part of p-toluenesulfonic acid and then heated under reflux for 4 hours, whereafter the methanol is distilled off. The residue is taken up in ether and is washed with aqueous sodium bicarbonate and water, and the ether is distilled off. Distillation produces a first fraction boiling at 210°–240° C./0.5 mbar and containing the compound of Example 1a.

A second fraction boiling at 240–290° C./0.5 mbar contains a mixture of 2,6- and 2,7-bis(5-carboxy-2-methyl-pent-2-yl)anthracene. Fractional crystallization from methanol produces the pure crystalline 2,6- and 2,7-isomers having melting points of 111°–113° C. and 94°–96° C. respectively.

(b) 5 parts of a 2,6- isomer, dissolved in 25 parts of glacial acetic acid, are heated on a steam bath. To the solution are added 3 parts of chromium trioxide, dissolved in a mixture of 3 parts of water and 10 parts of glacial acetic acid, in the course of 30 minutes. This is followed by a further 30 minutes of heating on the steam bath and dilution with water. This is followed by extraction with ether, washing of the ether solution with water and evaporation of the ether. The oily residue is digested with methanol, and the crystalline precipitate is filtered off and dried. This gives 2,6-bis(5-methoxycarbonyl-2-methyl-pent-2-yl)anthraquinone having a melting point of 102°–104° C.

(c) Alkaline hydrolysis produces 2,6-bis(5-carboxy-2-methyl-pent-2-yl)anthraquinone having a melting point of 222°–224° C. (recrystallization from acetic acid).

EXAMPLE 6

2,7-Bis(5-carboxy-2-methyl-pent-2-yl)anthraquinone (a) The 2,7- isomer obtained as per Example 5a is oxidized as described in Example 5b and isolated to give 2,7-bis(5-methoxycarbonyl-2-methyl-pent-2-yl)anthraquinone as a yellow viscous oil.

| Elemental analysis (% by weight): | | |
|---|---|---|
| | C | H |
| Found: | 73.51 | 7.22 |
| Calculated: | 73.15 | 7.37 |

(b) Alkaline hydrolysis produces 2,7-bis(5-carboxy-2-methyl-pent-2-yl)anthraquinone having a melting point of 145°–147° C. (recrystallization from ether).

EXAMPLE 7

Methyl 3-(2'-anthraquinoyl)-3-methylbutanecarboxylate (a) 11.4 parts of methyl 3-methylcrotonate are added dropwise to a stirred suspension of 13.3 parts of aluminium trichloride in 78.1 parts of benzene in the course of one hour, during which the temperature is maintained between 25° and 30° C. The homogeneous solution formed is subsequently stirred at that temperature for a further 6 hours and then poured into 400 parts of water. The oil formed is extracted with ether, the extract is washed with water, the ether is evaporated, and the residue is distilled to give methyl 3-phenyl-3-methylbutanecarboxylate.

(b) To 19.2 parts of this compound and 5 parts of carbon disulfide are added 14.8 parts of phthalic anhydride and 40.2 parts of aluminium chloride. The mixture is heated under reflux for 20 hours. Sufficient water is added to destroy the AlCl₃ complex, which is followed by extraction with ether. The extract is washed with water, the ether is distilled off, the residue is taken up in a mixture of toluene and petroleum ether, and the crystalline precipitate is filtered off and dried. This gives 2-carboxy-4'-(3-methoxycarbonyl-2-methyl-prop-2-yl)-benzophenone having a melting point of 118°–120° C.

(c) 3.4 parts of this compound are suspended in 50 parts of carbon disulfide and 1.2 parts of thionyl chloride and the suspension is heated under reflux for 2 hours. After the acid has dissolved, 1.3 parts of aluminium trichloride are added, and the mixture is heated under reflux for a further 20 hours. Addition of water is followed by extraction with ether and washing of the extract with water and aqueous sodium bicarbonate and again with water. The ether is distilled off, and the residue is taken up in a mixture of ether and 40°–60° C. petroleum ether. The crystalline precipitate is filtered off and dried. This gives methyl 3-(2'-anthraquinoyl)-3-methylbutanecarboxylate having a melting point of 103°–105° C.

EXAMPLE 8

Methyl 5-(2'-anthraquinoyl)-5-methylhexanecarboxylate (a) 300 parts of 98% sulfuric acid, 64 parts of methanol, 71 parts of methyl 5-methylhex-5-enecarboxylate and 53 parts of o-xylene are stirred at room temperature for 3 days and then poured into 2000 parts of water. This is followed by extraction with ether, washing of the extract with water and evaporation of the ether. The residue is dissolved in 500 parts of methanol, one part of p-toluenesulfonic acid, and the mixture is heated under reflux for 6 hours. The methanol is then distilled off, and the residue is taken up in ether and washed first with aqueous sodium bicarbonate and then with water. The ether is evaporated off and the residue is distilled to give methyl 5-(3,4-dimethylphenyl)-5-methylhexanecarboxylate having a boiling point of 176°–182° C./16 mbar.

| Elemental analysis (% by weight): | | |
|---|---|---|
| | C | H |
| Found: | 77.85 | 9.57 |
| Calculated: | 77.38 | 9.74 |

(b) Alkaline hydrolysis of this ester produces 5-(3,4-dimethylphenyl)-5-methylhexanecarboxylic acid having a melting point of 71°–73° C. (recrystallization from petroleum ether).

(c) To a stirred solution of this compound under reflux in 600 parts of water and 10.1 parts of KOH are added, portionwise, 158 parts of KMnO₄ in the course of 3 hours. After a further hour of refluxing, the mixture is cooled down and the MnO₂ which is formed is filtered off. The filtrate is acidified with hydrochloric acid and evaporated to dryness in a rotary evaporator under reduced pressure, and the residue is extracted with acetone. The extract is filtered, the acetone is evaporated off, and the residue is taken up in a mixture of ethyl acetate and 40°–60° C. petroleum ether. The crystalline precipitate is filtered off and dried. This gives 4-(5-carboxy-2-methyl-pent-2-yl) phthalic acid having a melting point of 154°–158° C.

(d) 23.5 parts of this compound are stirred at 225° C./20 mbar for 3 hours, cooled down and taken up in a mixture of 40°–60° C. petroleum ether and benzene. This gives 4-(5-carboxy-2-methyl-pent-2-yl) phthalic anhydride having a melting point of 140°–143° C.

(e) 3.5 parts of this anhydride and 50 parts of benzene are heated to reflux, and 5 parts of aluminium trichloride are added portionwise in the course of one hour. After a further 3 hours of heating, dilute hydrochloric acid is added. The oil which is formed is extracted with ether, the solution is washed with water, the ether is evaporated and the residue is dissolved in 50 ml of 30% oleum. After 4 days the solution poured into 500 parts of water and extracted with ether. The extract is washed with water, and the residue is esterified with methanol to give methyl 5-(2'-anthraquinoyl)-5-methylhexanecarboxylate having a boiling point of 200° C./0.06 mbar and a melting point of 70°–72° C. (recrystallized from ether/petroleum ether). The compound is identical to the compound of Example 1b.

EXAMPLE 9

5-(2'-Anthraquinoyl)-5-methylhexanecarboxylic acid (a) Methyl 5-methyl-5-phenylhexanecarboxylate having a boiling point of 165°–170° C./16 mbar is prepared by reacting 14.2 parts of methyl 5-methylhex-5-enecarboxylate, 13.4 parts of aluminium trichloride and 39 parts of benzene in the manner of Example 7a.

(b) 11 parts of this compound, 7.4 parts of phthalic anhydride, 20.1 parts of aluminium trichloride and 25 parts of carbon disulfide are reacted and worked up in the manner of Example 7b to give 2-carboxy-4'-(5-methoxycarbonyl-2-methyl-pent-2-yl)-benzophenone having a melting point of 138°–140° C. (recrystallization from ether).

(c) Alkaline hydrolysis produces 2-carboxy-4'-(5-carboxy-2-methyl-pent-2-yl)-benzophenone having a melting point of 169°–171° C.

(d) 0.5 part of this compound is dissolved in 5 parts by volume of 30% oleum and set aside for 61 days. After pouring into water, the yellow solid is filtered off, washed with water, dried and crystallized from ether/40°–60° C. petroleum ether. The product obtained is 5-(2'-anthraquinoyl)-5-methylhexanecarboxylic acid having a melting point of 122°–124° C., which is identical to the acid of Example 1C.

EXAMPLE 10

5-(2'-Anthraquinoyl)-5-methylhexanecarboxylic acid (a) 13.6 parts of anhydrous zinc chloride are dissolved in 20.4 parts of concentrated hydrochloric acid, and 39.4 parts of 2-aminobenzophenone and 25.6 parts of 5-methylhex-5-enecarboxylic acid are added. The mixture is heated at 150° C. in a Carius vessel for 48 hours. After cooling down, 500 parts of methanol are added, and the mixture is heated under reflux for 4 hours. Excess methanol is distilled off. The residue is treated with 200 parts of ammonia (0.88) in 200 parts of water. Extraction with ether and distillation gives a fraction boiling at 200°–244° C./0.8 mbar. This fraction is refluxed together with 25 parts of NaOH in 250 parts of water for 5 hours. After cooling down, the insoluble oil is separated off. The alkaline hydrolysis solution is acidified with concentrated hydrochloric acid, and the solid precipitate is filtered off. The product obtained is 2-amino-5-(5'-carboxy-2'-methylpent-2'-yl)-benzophenone having a melting point of 101°–103° C. (recrystallization from 40°–60° C. petroleum ether containing a little ether).

(b) This acid is esterified with methanol which has been saturated with HCl gas to give 2-amino-5-(5'-methoxycarbonyl-2'-methylpent-2'-yl)-benzophenone.

| Elemental analysis (% by weight): | | | |
|---|---|---|---|
| | C | H | N |
| Found: | 74.39 | 7.54 | 4.06 |
| Calculated: | 74.31 | 7.42 | 4.13 |

(c) 6 parts of this ester are dissolved in 20 parts of acetone, and the solution is stirred and cooled down to 5° C. In the course of 1 hour, 10.2 parts of concentrated hydrochloric acid are added dropwise, followed by 2.5 parts of sodium nitrite dissolved in 5 parts of water. After a further hour of stirring 20 parts of water are added. The solution is then added dropwise to a hot solution of 9.2 parts of CuCN and 9.8 parts of NaCN in 4 parts of water at 60° C. in the course of 1 hour. Stirring is continued at 75° C. for 2 hours. This is followed by extraction with ether, evaporation of ether and chromatography over silica with 40°–60° C. petroleum ether. Elution with petroleum ether and increasing amounts (up to 25% by volume) of ether gives 2-cyano-5-(5'-methoxy-carbonyl-2'-methylpent-2'-yl)-benzophenone.

| Elemental analysis (% by weight): | | | |
|---|---|---|---|
| | C | H | N |
| Found: | 75.63 | 6.59 | 3.83 |
| Calculated: | 75.62 | 6.53 | 4.01 |

(d) To 1.9 parts of this nitrile are added 5 parts of glacial acetic acid, 5 parts of water and 10 parts of 98% sulfuric acid, and the mixture is refluxed for 6 hours. The product is isolated and recrystallized from ethyl acetate/40°–60° C. petroleum ether. 2-Carboxy-5-(5'-carboxy-2'-methyl-pent-2'-yl)-benzophenone is obtained with a melting point of 178°–181° C.

(e) 0.5 part of this acid is dissolved in 7.5 parts of 30% oleum and set aside at room temperature for 4 days. The reaction mixture is then poured into water, and the precipitate is filtered off, washed, dried and recrystallized from ether to give 5-(2'-anthraquinoyl)-5-methylhexanecarboxylic acid having a melting point of 123°–124° C., which is identical to the compound of Example 1c.

EXAMPLE 11

5-(2'-Anthraquinoyl)-5-methylhexanecarbohydrazide

A mixture of 43.3 g of methyl 5-(2'-anthraquinoyl)-5-methylhexanecarboxylate prepared as in Example 1b, 26 ml of hydrazine hydrate and 200 ml of ethanol is refluxed under argon for 22 hours. The mixture is poured onto 400 ml of ice-water and extracted with 500 ml of chloroform. The organic phase is washed with water, dried and evaporated. Chromatography of the residue over silica gel (1 kg) using 40:3 dichloromethane/ethanol as eluent gives 41 g of 5-(2'-anthraquinoyl)-5-methylhexanecarbohydrazide.

Mass spectrum (indirect sample feed, 205° C.): m/e=350 (M+, 100%).

EXAMPLE 12

5-(Anthraquinon-2'-yl)-5-methylhexanecarbo-N-1-methylhydrazide

To a solution of 6.7 g of 5-(anthraquinon-2'-yl)-5-methylhexanecarboxylic acid prepared as in Example 1c in 30 ml of dry tetrahydrofuran (THF) are added at −15° C. under argon, 2.5 g of N-methylmorpholine and 3.0 g of isobutyl chloroformate. This is followed after 10 minutes by 1.85 g of N-methylhydrazine in 20 ml of THF. The mixture is warmed to room temperature and stirred at that temperature for 30 minutes. The tetrahydrofuran is evaporated off, and the residue is dissolved in ethyl acetate and washed with 5% aqueous sodium bicarbonate solution. The residue of the organic phase (8.1 g) is purified by chromatography over 1 kg of silica gel. Elution with 4/1 methylene chloride/ethyl acetate gives 4.8 g of hydrazide. Mass spectrum (indirect sample feed, 205° C.): m/e=364 (20%, M+), 46 (100%).

| Elemental analysis (% by weight): | | | | |
|---|---|---|---|---|
| | C | H | N | O |
| Calculated: | 72.0 | 6.7 | 7.4 | 13.7 |
| Found: | 72.5 | 6.64 | 7.68 | 13.17 |

EXAMPLE 13

5-(2'-Anthraquinoyl)-5-methyl-N,N-di-(4''-hydroxyphenyl)-hexanecarboxamide (a) 5-(2'-Anthraquinoyl)-5-methylhexanecarbonyl chloride.

To a solution of 4.06 g of 5-(2'-anthraquinoyl)-5-methylhexanecarboxylic acid as prepared in Example 1c in 20 ml of thionyl chloride is added 0.2 ml of N,N-dimethylformamide. This is followed by stirring at room temperature for 30 minutes, and the reagent is distilled off under atmospheric pressure. Drying of the residue under a high vacuum gives 5.0 g of crystalline acid chloride, which can be used without further purification.

(b) 5-(2'-Anthraquinoyl)-5-methyl-N,N-bis-(4''-acetoxyphenyl)hexanecarboxamide

A solution of 1.04 g of 5-(2'-anthraquinoyl)-5-methylhexanecarbonyl chloride as per Example 13a, 558 mg of 4,4'-diacetoxydiphenylamine [CA 90, 22577d (1979)] and 267 mg of p-N,N-dimethylaminopyridine in 3 ml of pyridine is stirred at room temperature for 4 days. This is followed by taking up in dichloromethane and washing with 2N hydrochloric acid and saturated sodium chloride solution. Chromatography of the residue of the organic phase over silica gel using 9:9:2 dichloromethane/toluene/diethyl ether as eluent gives 590 mg of 5-(2'-anthraquinoyl)-5-methyl-N,N-bis-(4''-acetoxyphenyl)-hexanecarboxamide. Mass spectrum (indirect sample feed, 270° C.): m/e=603 (M+, 40%), 285 (60%), 243 (90%), 201 (100%).

(c) 5-(2'-Anthraquinoyl)-5-methyl-N,N-di-(4''-hydroxyphenyl)hexanecarboxamide

A mixture of 358 mg of diacetate as per Example 13b, 10 ml of methanol, 3 ml of dichloroethane and 0.1 ml of methanesulfonic acid is refluxed for 45 minutes. Diluting with dichloromethane, washing with water and saturated sodium chloride solution, drying and evaporation of the organic phase and chromatography of the residue over silica gel using 3:1 chloroform/ethyl acetate as eluent gives 290 mg of 5-(2'-anthraquinoyl)-5- methyl-N,N-di-(4″-hydroxyphenyl)-hexanecarboxamide. Mass spectrum (indirect sample feed, 320° C.): m/e=519 (M+, 1%).

(B) APPLICATION EXAMPLES
EXAMPLE 14

(a) 173.3 g (0.5 mol) of bisphenol-A diglycidyl ether are dissolved in 180 ml of ethylene glycol monoethyl ether at 40° C. To this solution are added dropwise with stirring 15.3 g (0.25 mol) of ethanolamine, the temperature is raised to 60° C., and reaction is allowed to proceed for a further 3 hours. The result obtained is a viscous solution. The epoxy equivalent of this solution is 1.158 mol of epoxide/kg (determined by the method of R. R. Jay, Analytical Chemistry 36 (1964) 667). This corresponds to an average molecular weight of the advancement product of 915 daltons.

5 g of the solution (5.79 mmol equivalent of epoxide) are reacted with 2.85 mmol of (2-anthraquinoyl)-5-methylhexanecarbohydrazide at 130° C. with stirring and under protective gas in the course of 2 hours. The result is a viscous solution having a low epoxy residue content. The solution is applied to a polyester base by means of wire-wound draw bars in the form of a film and is dried at 80° C. in a through-circulation oven for 12 hours.

(b) The procedure is repeated using other mixing ratios (see table). The table gives the properties of the polyadducts.

The photoefficiency of the photo reduction is determined as follows. A film on a polyester base having an optical density (O.D.) of 1 at 324 nm is irradiated with an Hg high pressure lamp with 40 mW/cm$^{-2}$, and the UV/VIS spectrum is recorded at regular intervals. The band at 324 nm decreases, while that at 386 nm increases. The ratio of the two bands after 2 minutes of exposure to light is taken as the photoefficiency.

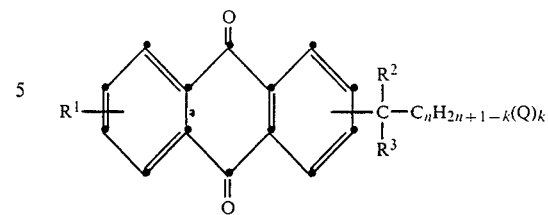

in which n is a number from 1 to 17, k is 1 or 2 and Q is —COOH or —CONR$^4$—NH$_2$ or k is 1 and Q is —OH, —NHR$^4$, —OCOR$^5$, —N(R$^4$)COR$^5$ or

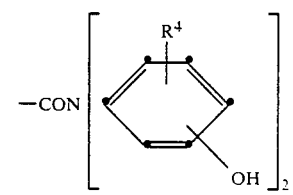

in which R$^4$ is H or C$_1$–C$_4$-alkyl and R$^5$ is a monodecarboxylated radical of a tricarboxylic acid or tetracarboxylic acid, R$^2$ and R$^3$ are independently of each other linear or branched C$_1$–C$_5$-alkyl which is unsubstituted, or, substituted by —COOH or —CONR$^4$—NH$_2$ only if Q is —COOH or —CONR$^4$—NH$_2$, or R$^2$ together with the C$_n$H$_{2n+1-k}$ group forms C$_5$–C$_{12}$cycloalkylene and R$^3$ is C$_1$–C$_5$-alkyl, and R$^1$ is H, linear or branched C$_1$–C$_8$-alkyl, unsubstituted or monohalogenated or dihalogenated C$_7$–C$_9$-aralkyl, unsubstituted or C$_1$–C$_4$-alkyl-substituted C$_5$–C$_{12}$-cycloalkyl, or a radical of the formula —CR$^2$R$^3$—C$_n$H$_{2n+1-k}$(Q)$_k$.

2. A compound according to claim 1, where, in the formula I, R$^1$ is H or a radical of the formula

|  |  | mmol of starting substances |  | Content in adduct of |  | Photo |
|---|---|---|---|---|---|---|
| Example No. | Tg °C. | Compound as per Example 12 | Ethanolamine | Bisphenol-A diglycidyl ether | Anthraquinone (mmol/kg) | OH (mmol/kg) | efficiency O.D. 324 nm O.D. 386 nm |
| a | 86 | 1 | 1 | 2 | 0.77 | 3.86 | 0.53 |
| b | 101 | 1 | 2 | 3 | 0.18 | 3.44 | 0.67 |

Photometallization

Films on a polyester base are exposed at 50° C. on a thermostatable vacuum hot bench with an Hg high pressure lamp with an intensity of 40 mW/cm$^{-2}$ through a negative.

The result obtained is a dark, negative image of the original which is enhanced at 45° C. in a deposition bath of the composition:

| CuSO$_4$ × 5H$_2$O | 0.0665 mol/l |
|---|---|
| HCOH | 0.0467 mol/l |
| Quadrol | 0.0599 mol/l |
| NaOH | pH 12.6 |
| NaCN | 25 mg/l |
| 2-Mercaptobenzothiazole | 10 mg/l | to give a metallic copper image.

What is claimed is:

1. A compound of the formula I

—CR$^2$R$^3$C$_n$H$_{2n+1-k}$(Q)$_k$, R$^2$ and R$^3$ are independently of each other methyl or ethyl, n is a number from 1 to 8, k is 1, Q is —COOH or —CONR$^4$—NH$_2$, and R$^4$ is H or C$_1$–C$_4$-alkyl.

3. A compound according to claim 1, where, in the formula I, k is 1, n is a number from 1 to 12, and Q is as defined in claim 1.

4. A compound according to claim 1, where, in the formula I, R$^1$ is H or a radical of the formula —CR$^2$R$^3$—C$_n$H$_{2n+1-k}$(Q)$_k$.

5. A compound according to claim 1, where, in the formula I, the radical —CR$^2$R$^3$C$_n$H$_{2n+1-k}$(Q)$_k$ is bonded in the 2-position and the radical R$^1$ is bonded in the 6- or 7-position.

6. A compound according to claim 5, wherein R$^1$ is —CR$^2$R$^3$C$_n$H$_{2n+1-k}$(Q)$_k$.

7. A compound according to claim 1, wherein Q is —CONR$^4$—NH$_2$ and R$^4$ is H or methyl.

8. A compound of the formula Ia

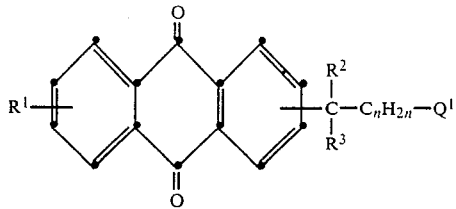

in which $R^1$ is H, linear or branched $C_1$–$C_8$-alkyl, unsubstituted or monohalogenated or dihalogenated $C_7$–$C_9$-aralkyl, unsubstituted or $C_1$–$C_4$-alkyl-substituted $C_5$–$C_{12}$-cycloalkyl or a radical of the formula —$CR^2R^3$—$C_nH_{2n}$—$Q^1$; $R^2$ and $R^3$ are independently of each other linear or branched $C_1$–$C_5$-alkyl, or $R^2$ combines with the $C_nH_{2n}$ n group to form $C_5$–$C_{12}$ cycloalkylene and $R^3$ is H or $C_1$–$C_5$-alkyl; n is a number from 1 to 17, and $Q^1$ is —CN, —COCl, —CONHR$^4$, —CON(R$^4$)$_2$, —COR$^6$, —O—$C_1$–$C_8$-acyl or —NR$^4$—$C_1$–$C_8$-acyl in which $R^4$ is H or $C_1$–$C_4$-alkyl and $R^6$ is a radical of a monohydric alcohol.

* * * * *